United States Patent
Nemirovski (10) Patent No.: US 6,503,197 B1
(45) Date of Patent: Jan. 7, 2003

(54) SYSTEM AND METHOD FOR DETECTING AN ACTION OF THE HEAD AND GENERATING AN OUTPUT IN RESPONSE THERETO

(75) Inventor: Guerman G. Nemirovski, St. Petersburg, FL (US)

(73) Assignee: Think-A-Move, Ltd., Beachwood, OH (US)

(*) Notice: Subject to any disclaimer, the term of this patent is extended or adjusted under 35 U.S.C. 154(b) by 66 days.

(21) Appl. No.: 09/706,091

(22) Filed: Nov. 3, 2000

Related U.S. Application Data (60) Provisional application No. 60/164,360, filed on Nov. 9, 1999.

(51) Int. Cl.⁷ .................................................. A61B 5/00
(52) U.S. Cl. ........................ 600/300; 128/898; 128/920; 128/925; 600/587; 704/271
(58) Field of Search ................................ 600/379, 383, 600/372, 559, 561, 587, 590, 595, 300–301; 607/136, 55–57, 312–314, 320–321, 323, 68; 381/23.1, 60; 128/898, 920, 925; 704/271

(56) References Cited

U.S. PATENT DOCUMENTS

| | | | |
|---|---|---|---|
| 3,870,034 A | | 3/1975 | James |
| 4,064,870 A | | 12/1977 | Dumitrescu et al. |
| 4,429,702 A | | 2/1984 | von Recklinghausen |
| 4,652,702 A | | 3/1987 | Yoshii |
| 5,149,104 A | | 9/1992 | Edelstein |
| 5,604,812 A | * | 2/1997 | Meyer .................. 381/68.2 |
| 5,638,826 A | | 6/1997 | Wolpaw et al. |
| 5,676,138 A | | 10/1997 | Zawilinski |
| 5,812,978 A | | 9/1998 | Nolan |
| 5,878,396 A | | 3/1999 | Henton |
| 6,024,700 A | | 2/2000 | Nemirovski et al. |
| 6,044,163 A | * | 3/2000 | Weinfurtner ........... 381/312 |
| 6,175,633 B1 | | 1/2001 | Morrill et al. |
| 6,283,915 B1 | | 9/2001 | Aceti et al. |
| 6,289,247 B1 | * | 9/2001 | Faltys ..................... 607/57 |

FOREIGN PATENT DOCUMENTS

| | | |
|---|---|---|
| CH | 678692 A5 | 10/1991 |
| EP | 0 501 058 A2 | 9/1992 |
| EP | 0 767 414 A1 | 4/1997 |
| WO | WO 00/03639 | 1/2000 |

OTHER PUBLICATIONS

*Detection of Sensorineural Hearing Impairment By Using DPOAE Technique and Classifiers*, A. Nevcihan, et al., 1995 IEEE–EMBC and CMBEC, Theme 4: Signal Processing, 0–7803–2475–7/97.

Sound Radio Products™ Better Living Through Wireless Technology, printed Oct. 29, 2001 from Internet Website http://www.soundradio.com/en–921.html.

(List continued on next page.)

*Primary Examiner*—Kevin Shaver
*Assistant Examiner*—Michael Astorino
(74) *Attorney, Agent, or Firm*—Renner, Otto, Boisselle & Sklar, LLP

(57) ABSTRACT

A method of producing a control signal. The method includes the steps of sensing an air pressure pattern in or near an ear of a person, the air pressure pattern resulting from voluntary physical action of the person; and converting the air pressure pattern into an output signal. Also described is a control system. The control system includes an air pressure sensor for detecting an air pressure pattern adjacent an ear of a person while the person makes a voluntary physical action and for producing an output signal corresponding to the detected air pressure pattern; and processing circuitry for discerning a pattern from the output signal.

31 Claims, 6 Drawing Sheets

OTHER PUBLICATIONS

"Answering Questions With an Electroencephalogram–Based Brain–Computer Interface", by Laurie A. Miner, MS, PT; Dennis J. McFarland, PhD.; and Jonathan R. Wolpaw, MD, Reprinted from the Internet at http://www.archives–pmr.prg/abs79_9/v9n9p1029.html and http://silk.nig.gov/silk/nc–mrr/abstract/absJRW1.htm, 3 pages.

"Brain Actuated Technologies", Reprinted by Andrew M. Junker, PhD., from the Internet at http://www.mindmouse.com/Business.bat.htm, Dec. 4, 1998, 2 pages.

"Discover the Cyberlink™ Mind Mouse!", Reprinted from the Internet at http://mindmouse.com, Dec. 4, 1998, 1 page.

"The Cyberlink™ Mind Mouse", Reprinted from the Internet at http://mindmouse.com/Business/Productinfo.htm, Dec. 4, 1998, 2 pages.

*Devices read brain waves* "They help paralyzed communicate", by Robert S. Boyd, taken from the Internet at http://www.free.com/tech/qthink25.htm, 4 pages.

"The MindDrive Thought Response Technology", *The Other 90*, Reprinted from the Internet at http://www.other90.come/new/htm/whitepage.htm, Jul. 9, 1998, 2 pages.

* cited by examiner

SYSTEM AND METHOD FOR DETECTING AN ACTION OF THE HEAD AND GENERATING AN OUTPUT IN RESPONSE THERETO

CROSS-REFERENCE TO RELATED APPLICATION(S)

This application claim priority from U.S. provisional patent application Ser. No. 60/164,360 filed Nov. 9, 1999 and titled "System and Method for Detecting an Action of the Head and Generating an Output in Response Thereto", the disclosure of which is incorporated herein by reference in its entirety.

FIELD OF THE INVENTION

The present invention generally relates to detecting actions of the head of a person such as muscle firings, movements, movement of the tongue with respect to the oral cavity, etc. using a sensor and providing an output, for example, system control functions, in response to such detection. More particularly, the present invention detects motions, positions and actions of the tongue in the oral cavity by analyzing changes in air pressure near the human ear and processing the collected data to determine a proper control functionality corresponding thereto.

BACKGROUND OF THE INVENTION

An apparatus and method for detecting thoughts is disclosed in U.S. Pat. No. 6,024,700, the entire disclosure of which is incorporated by reference. Such system and method may require concentration to develop the same thought consistently and to have that thought detected consistently. Training may be required to obtain the desired concentration and consistency. Such concentration may be relatively taxing. The thought may lead to a detectable air pressure or sound at one or both ears of a user of such system and method, and such air pressure can be detected by a detector, such as a microphone. Exemplary outputs from such system and method for detecting thoughts may be one or plural discrete outputs, such as discrete outputs representing respective alphanumeric characters, directions, etc.

Sounds produced by a person's ears sometimes are referred to as autoaccoustic. Autoaccoustic sounds have been used in the past for diagnostics, e.g., to indicate ear function or a condition of the ear. For example, in response to a sound input to the ear, the ear has been found to provide a detectable autoaccoustic output.

At present there are available controllers to enable a handicapped person, who cannot use arms or legs, to operate a motorized wheelchair. Such a controller includes a trackball or joystick type device that is inserted into the mouth of an individual; and the individual operates the controller using mouth and/or tongue movements to provide mechanical inputs. Such device is difficult to operate and is problematic if it falls from the mouth or irritates the mouth.

Other controllers exist to enable handicapped individuals to perform functions with mechanical assists. Operation of such controllers typically requires a signal, such as an incident electromagnetic signal, e.g., infrared or ultraviolet light/radiation, which is directed at the individual; then, by a specified action or activity the individual can modulate the incident electromagnetic signal, e.g., by blinking the eyes, moving the head, or some such action. The need for incident electromagnetic signal is disadvantageous for several reasons: An extra piece of equipment is required to provide that signal, the signal must be properly directed or aligned, the detector and the modulated signal must be properly aligned, the signal should not have a detrimental affect on the user (such as causing eye injury), etc.

SUMMARY OF THE INVENTION

According to one aspect of the invention, the invention is a method of producing a control signal. The method includes the steps of sensing an air pressure pattern in or near an ear of a person, the air pressure pattern resulting from voluntary physical action of the person; and converting the air pressure pattern into an output signal.

According to another aspect of the invention, the invention is a method of detecting a voluntary motion of a person by monitoring air pressure near an ear of the person.

According to another aspect of the invention, the invention is a control system. The control system includes an air pressure sensor for detecting an air pressure pattern adjacent an ear of a person while the person makes a voluntary physical action and for producing an output signal corresponding to the detected air pressure pattern; and processing circuitry for discerning a pattern from the output signal.

DETAILED DESCRIPTION OF THE INVENTION

The following is a detailed description of the present invention made in conjunction with the attached Figures, wherein like reference numerals will refer to like elements throughout.

The present invention is directed to apparatus and method for detecting actions of the head of a person, such as actions occurring in association with the oral cavity, wherein those actions may provide not only discrete outputs but also may produce a range of outputs, as in an analog type signal. As an example, motion of the tongue in the oral cavity, for example, two-dimensional motion or three-dimensional motion, can be detected or sensed to provide a useful output. An exemplary output may be in the form of a signal analogous to that produced by a computer mouse, the click buttons on the mouse, a computer joystick, or the like.

Using the present invention has been found somewhat less taxing and usually requires less concentration than the above-mentioned thought detection apparatus and method. Also, the present invention is able to provide an output having a continuity characteristic, e.g., similar to the signal produced by moving a computer mouse along a surface. Still further, since the tongue is able to move in three dimensions, the invention is able to provide a three dimensional type signal output such as that produced by a computer joystick that has up, down, left, right, front and back signal outputs with speed characteristics of the signal being related to the speed at which the joystick is moved to respective locations or in respective directions.

The invention may be used for many purposes. One exemplary use is to provide an input to a computer or to some other electrical or electronic device. An exemplary input is an electrical signal, but it will be appreciated that the input may be other than electrical, for example, optical, fluidic, etc. The input may control the computer or other device or it may be used for some other purpose. To facilitate and to avoid complexity of the description of the invention herein, the invention is described with respect to a use to provide an electrical input to a computer, for example, a personal computer or some other computer, whether of the digital or analog type, to control the operation of the computer. It will be appreciated that the invention may be used for many other purposes.

One example of a use of the invention in combination with a computer which is controlled using the invention is to provide functions and capabilities for a handicapped person. For example, the invention may be used to enable a handicapped individual or a non-handicapped individual to control operation of a piece of machinery in a manufacturing facility, to control operation of a motorized wheelchair or similar device, to control operation of, e.g, to play, a video game, etc. These are only examples, and it will be appreciated that the invention may be used for many other purposes.

In the present invention there is no need for incident electromagnetic signals which require modulation to produce a useful output. Rather, in the present invention actions of the individual occurring in the head of the individual, for example, with respect to the oral cavity, such as tongue movement, clicking of the tongue against the teeth or pallet, etc., are used to create air pressure or sounds at one or both ears of the individual, which can be detected or sensed and used as an output of the invention to be provided as an input to a computer or to some other device. Thus, the present invention presents an unstimulated signal, e.g., a signal that is produced by action of the individual without the need for an incident input, such as an incident electromagnetic signal.

In accordance with an embodiment of the invention a sensor senses or detects air pressure or a change in air pressure or a sound that is produced by an ear of an individual. To facilitate the description herein, the event of sensing or detecting will be referred to as detecting and that which is detected will be referred to as air pressure. Also, to facilitate the description herein, the action causing the detectable air pressure will be described as movement of the tongue in the oral cavity, sometimes referred to as "tongue action," although it will be appreciated that the invention contemplates that other muscle movements or actions in or associated with the oral cavity or even of the head itself, clicking or other actions of the tongue against the teeth or pallet, exhaling or inhaling by the lungs, actions of the nose, which lead to detectable air pressure at the ear or ears of the individual may be used in accordance with the invention. Other detectable actions of the head may be rotating the head or tilting the head. An exemplary advantage of using tongue movements to lead to the detectable air pressure, is that tongue movement can be two dimensional or three dimensional—two being up and down or left and right movements, and three being a combination of front and back, left and right and up and down.

The present invention relates to a system and a method of detecting actions of the human head, in the example below the action being movement or other actions of the tongue with respect to the oral cavity, and providing a useful output in response to such detection. The present invention monitors changes in air pressure near the human ear which occur nearly instantaneously in response to the tongue action to provide a substantially real-time detection and control system. In addition, the monitoring of the air pressure is passive and thus avoids potential health and/or environmental concerns related to subjecting the body to electrical signals and radiation. Furthermore, the changes in air pressure uniquely correspond to one of a variety of tongue actions (e.g., have unique signal signatures) which allows a plurality of different tongue actions to be detected and distinguished for a system requiring multiple control functions.

According to one aspect of the present invention, a system for detecting a tongue action and providing a corresponding output in response to the detection includes a pressure sensor which is positioned near the ear of the user. The sensor is in electrical communication with processing circuitry and senses changes in air pressure near the ear due to the user's tongue actions and converts the air pressure changes into an electrical signal. The electrical signal is then processed by the circuitry to detect the presence and the type of tongue actions within the electrical signal and provide a control instruction or some other useful output, such as an output similar to that produced by a computer mouse or joystick which corresponds to the particular tongue action to an output peripheral for execution. Exemplary control functions may include, but are not limited to: controlling a video game display, controlling a piece of medical equipment such as a wheelchair, and controlling computer functions to effectuate a handless mouse, joystick, etc.

According to another aspect of the present invention, a method of detecting tongue actions and providing a control instruction corresponding to the tongue action is provided. Tongue actions are monitored by monitoring the air pressure wherein the air pressure changes near the ear correspond to tongue actions and noise. The method includes converting the air pressure data to an analog electrical signal which is subsequently converted into digital signal data for further processing. Data signal processing is implemented to analyze the data and to separate noise from tongue action data to thereby detect the presence of a tongue action. Further processing is then used to determine the type of tongue action detected and to provide one or more useful outputs, e.g., control instructions or some other output, to an output peripheral for execution of appropriate functions.

In an embodiment of the present invention, the pressure sensor and transducer includes a microphone and the data signal processing includes conversion of data segments into the frequency domain to distinguish data relating to a tongue action from noise. There also are a bandpass signal filtration function to separate noise which occurs at frequencies above and below a desired frequency or frequency range in which the signal is expected, and a power spectrum filtration to eliminate signals produced at power less than a threshold and, thus, are considered noise. Once a tongue action type signal is detected, further data processing includes feature extraction and then analysis of the feature to determine its correlation to stored features. If a satisfactory correlation is obtained, then the corresponding output is provided. The output may be, for example, one or more control instructions sent to an output peripheral for execution of the instructions, thereby providing system control functionality. A neural net may be used to carry out the correlation function.

Figure 1:
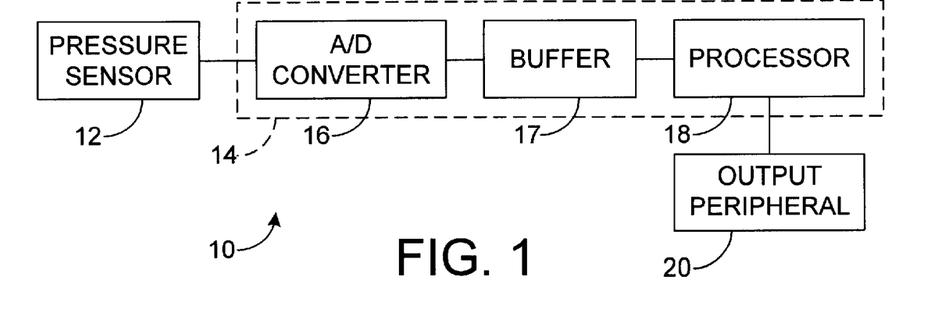
FIG. 1 is a block level diagram illustrating a system by which a mouth action also referred to herein sometimes as tongue action is detected and used to provide a control function which corresponds to the detected mouth action according to the present invention.

Turning now to the Figures, a detailed description of the invention follows. FIG. 1 is a block level diagram which illustrates a system 10 for detecting a tongue action or other head action and providing an output which corresponds to the detected tongue action. The system 10 includes a pressure sensor 12 coupled to processing circuitry 14 including an analog-to-digital (A/D) converter 16, such as a PCI9118HG data acquisition card manufactured by Adlink Technology or a DAQi250 data acquisition card manufactured by Ines Company Gmbh in Germany, for converting an analog signal into digital signal data. A buffer 17 is provided to store portions of signals from the A/D converter 16, as those signals may be relatively continuous, reflecting a continuing motion of the tongue, for example, until a filtration and signal detection can be carried out as are described further below. The processing circuitry 14 also includes a processor 18 for receiving the digital signal data from the A/D converter 16 and buffer 17 and performing various signal processing functions on the digital signal data to detect the occurrence of a tongue action and determine the type of tongue action. The system 10 also includes an output peripheral 20 coupled to the processor 18 for executing one or more control instructions provided by the processor 18 which correspond to the detected thought.

Figure 2A:
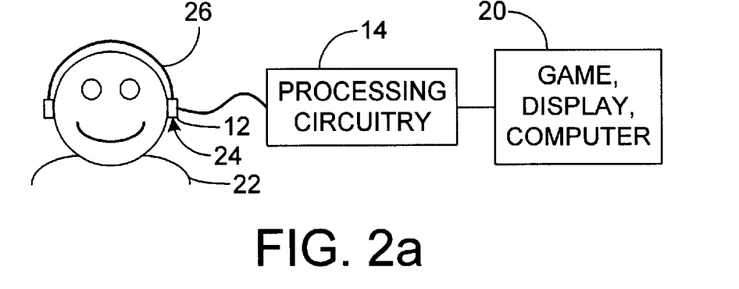
FIG. 2a is an environmental view of a user having a pressure sensor located near their ear which is in electrical communication with a processor coupled to a display according to the present invention.

The system 10 is illustrated within an exemplary environmental context in FIG. 2a. In FIG. 2a, a user 22 has the pressure sensor 12 located near the ear 24 by locating the pressure sensor 12 within a pair of headphones 26. The headphones 26 preferably provide two functions: (1) they locate the pressure sensor 12 near the ear in a relatively fixed position, and (2) they provide a modest amount of external sound insulation, thereby lessening the amount of external noise detected by the pressure sensor 12. When the user 22 acts by moving the tongue relative to the oral cavity, for example, a change in air pressure occurs in or near the ear 24, wherein the air pressure change uniquely identifies the tongue action. The change in air pressure is detected by the pressure sensor 12 which converts the detected air pressure into an analog electrical signal for subsequent processing by the circuitry 14. In FIG. 2a, the exemplary output peripheral 20 is illustrated as a display associated with a computer game or video game (or may provide a control function for a mechanized wheelchair, for carrying out a task in a manufacturing process, etc.) which carries out the control instruction (e.g., running, walking, flying, executing a punch or a kick in a video game, etc.). The direction and speed of motion displayed may correspond to the direction and speed of motion of the tongue and the strength of the kick or punch, for example, may correspond to the strength of clicking of the tongue against the pallet or teeth.

Figure 2B:
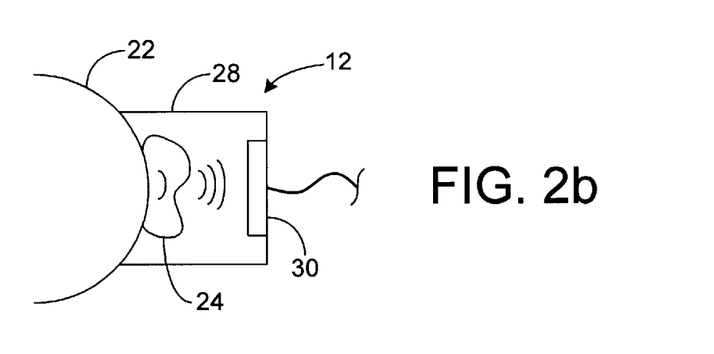
FIG. 2b is an enlarged view of a portion of FIG. 2a illustrating in greater detail the pressure sensor monitoring air pressure near the ear according to one aspect of the present invention.

The positional relationship between the pressure sensor 12 and the ear 24 is illustrated in greater detail in FIG. 2b. Although the invention may use a single sensor 12 as shown in FIG. 2b, use of two sensors as shown in FIG. 2a is advantageous to obtain three dimensional information whereby each sensor picks up different information as a function of three dimensional motion of the tongue with respect to the oral cavity or teeth or strength of the clicking of the tongue, etc. The detected signals may be correlated to provide an output that has in effect three degrees of motion, e.g., three dimensional effect. For example, movement in the oral cavity may be up and down, left and right, front and back, and respective combinations of such movements may provide the desired three dimensional result, whereby the sensors 12 at respective ears detect different air pressures, which can be correlated with three dimensional motion of a joystick or a mouse leading to output signals representing three dimensional motion.

The pressure sensor 12 includes a housing 28 such as a headphone housing which has a sensor, such as a microphone 30, affixed thereon. The manner in which the microphone 30 is attached to the housing 28 may vary in order to adjust the distance at which the microphone 30 is from the ear 24. The microphone 30 is near the ear 24, for example, within about 1 inch to 2 inches, depending upon the sensitivity of the microphone, however, other distances may also be used and are contemplated as falling within the scope of the present invention. The microphone 30 may be located comfortably within the ear 24 or as close as possible to the ear to receive the air pressure changes at an increased intensity level. In FIG. 2b neither the shape nor the position of the microphone 30 is drawn to scale, but rather is merely illustrated in this manner for the sake of clarity.

In an embodiment of the present invention, the microphone 30 has a sensitivity of at least about 47 mV/Pa (millivolts per pascal) and in an embodiment has a sensitivity of about 100 mV/Pa or more with a frequency range of about 10 Hz to about 800 Hz. A frequency range on the order of about 20 Hz is useful in an embodiment for detecting air pressure resulting from tongue action described herein. Also, it is noted here again that the reference to detecting air pressure may mean detecting air pressure, a difference in air pressure and/or sound. One exemplary microphone which may be used is the Model 4190 microphone manufactured by Brüel & Kjaer in Denmark. Alternatively, however, other types of microphone or other type pressure sensor may by used and each such alternative is contemplated as falling within the scope of the present invention. Using the Model 4190 microphone the analog output signal is about 400 mV peak-to-peak. The amplitude of the output signal, however, depends upon the amplitude coefficient of the electronics and the position of the microphone with respect to the ear and thus may vary substantially.

It is not certain what physical, chemical or neural mechanism causes or generates the changes in air pressure in or near the ear in response to various muscle firings, e.g., contraction and release of a muscle. However, due to the connection of the oral cavity to the ear via the eustachian tube, the movement of the tongue may cause an air pressure, a change in air pressure or an air flow to or from the ear leading to a detectable air pressure which can be detected by the sensor 12. Regardless of the exact physical, chemical or neural mechanism, empirical testing has confirmed that tongue actions generate pressure changes in or near the ear of the person and that the air pressure changes have substantially their own signature and are thus substantially unique for a given tongue action of an individual. Consequently, the air pressure changes can be monitored near the ear and used to detect the tongue action of a user.

Figure 2C:
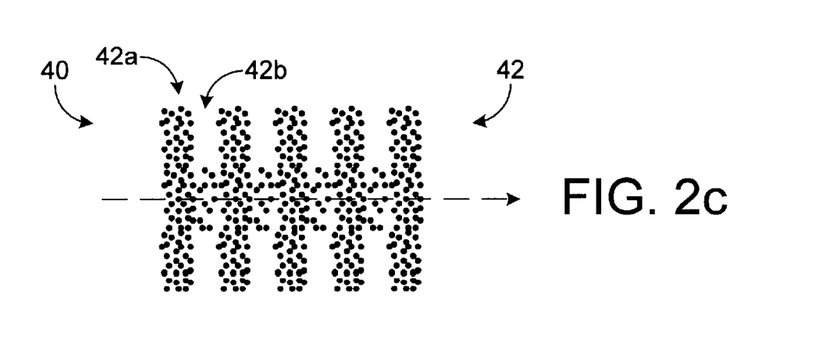
FIG. 2c is a pictorial representation of a wave in air, representing a plurality of longitudinal, molecular density changes according to the present invention.

The present invention uses the term "changes in air pressure" near the ear in its broadest sense to characterize the parameter being measured. Changes in air pressure may alternatively be characterized as sound waves. As is well known by those skilled in the art, a sound wave is a longitudinal wave in which "pushes" are communicated from molecule to molecule within the medium (which in this preferred embodiment is air). The restoring force for such a wave is due to the pressure of the air; wherever the density of molecules is higher than normal, the pressure also is higher than normal and pushes the molecules apart. FIG. 2c illustrates an exemplary sound wave 40 in air, and consists of a plurality of alternating zones 42 of low and high molecular density 42a and 42b, respectively. The varying molecular density results in changes in air pressure having a particular frequency as the sound wave propagates. In addition, as is well known by those skilled in the art, as a sound wave spreads out from its source, its intensity falls off because as the area of the wave grows larger, the total energy is constant. Therefore the energy per unit area decreases with the inverse square of the distance. Consequently, it is desirable to have the microphone 30 sufficiently close to the ear 24 so that the intensity level of the air pressure changes will be larger and thus easier to detect over any noise.

The frequency range at which sound waves are audible is about 20 Hz to about 20 KHz, however, the present invention is not concerned with whether the air pressure changes are audible since the microphone 30 is sufficiently sensitive and has a frequency detection range which is sufficient to detect air pressure changes at high or low frequencies. In an embodiment of the invention, a frequency range of about 10 Hz to about 800 Hz is focused upon since it has been determined via empirical testing that sufficient data is available within that frequency range to detect and identify tongue action. In another embodiment the frequency range is about 20 Hz plus or minus several Hz, e.g., plus or minus about 10 Hz., thus on the order of from about 10 Hz. To about 30 Hz. Alternatively, however, any frequency range may be monitored which is suitable to detect tongue action and such variations are contemplated as falling within the scope of the present invention.

Figure 2D:
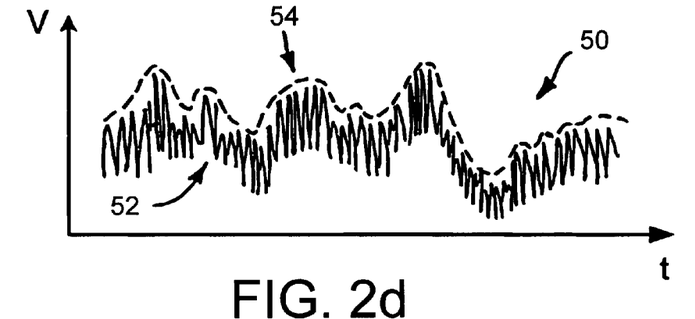
FIG. 2d is a graph illustrating an exemplary electrical signal produced by a transducer associated with the pressure sensor which indicates changes in air pressure at a location local to the pressure sensor according to the present invention.

The pressure sensor 12 (preferably including the microphone 30) monitors the changes in air pressure and converts the pressure data to an analog electrical signal 50, as illustrated in FIG. 2d. Note that in the signal 50 there are at least two signal components, a high frequency component 52 and a low frequency component 54. In addition, other frequencies may also exist within the electrical signal 50 and the present invention preferably analyzes the various signal frequencies in the subsequent data processing performed by the processor 18, which will be described in greater detail below.

Figure 3:
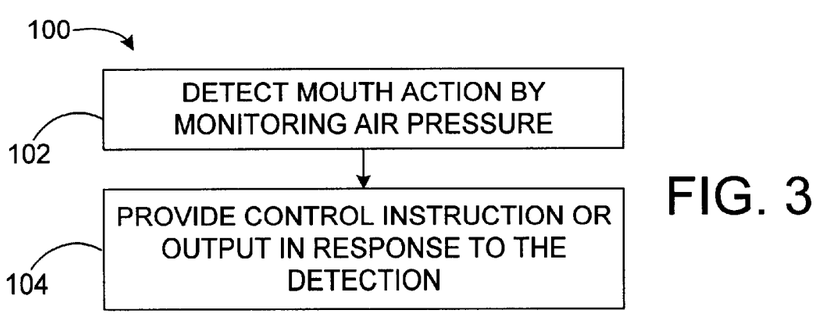
FIG. 3 is a flow chart diagram illustrating a method of detecting a mouth action and providing a control instruction in response to the detected mouth action according to the present invention.

A method 100 for carrying out the present invention is disclosed in FIG. 3. The method 100 includes detecting a tongue action by monitoring a change in air pressure caused by one's tongue actions at step 102. Once the tongue action is detected at step 102, one or more control instructions or other output(s) which correspond to the detected tongue action is provided to an output peripheral at step 104 to effectuate the desired output function.

Figure 4:
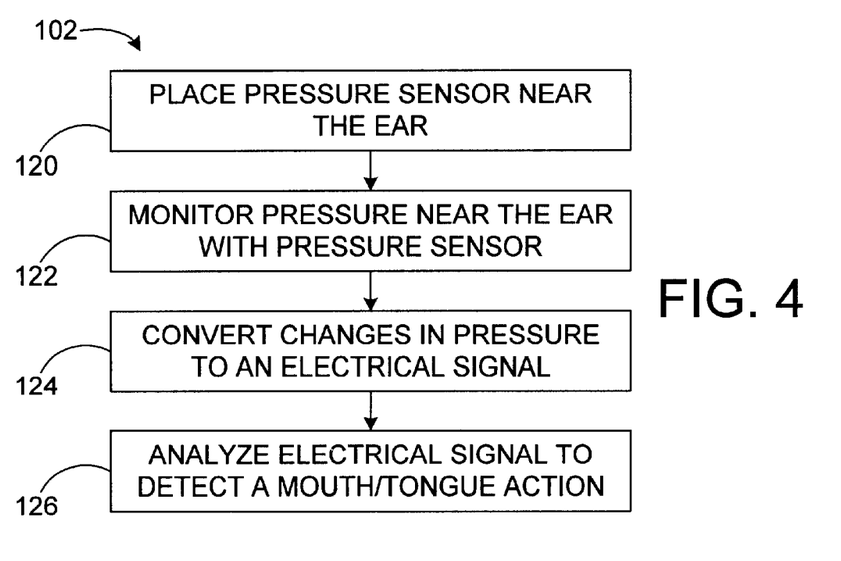
FIG. 4 is a flow chart diagram illustrating a method of monitoring the air pressure according to the present invention.

A method of detecting a tongue action (step 102) is illustrated in FIG. 4. A pressure sensor such as the one disclosed in conjunction with FIGS. 1 and 2a–2d is placed near the ear of the user who's tongue actions are to be detected at step 120. According to an embodiment of the present invention, air pressure changes near the ear occur in response to tongue actions and thus the pressure sensor is placed near the ear at step 120. Alternatively, however, since tongue actions may result in pressure changes at or near other parts of the body, it is contemplated that in alternative embodiments of the present invention the pressure sensor may be located on or near other parts of the body and any detection of tongue actions by analyzing changes in air pressure is contemplated as falling within the scope of the present invention.

The air pressure near the ear is monitored with the sensor at step 122 and is converted to an electrical signal at step 124 for subsequent analysis. After conversion into an electrical signal at step 124, the electrical signal is analyzed to detect a tongue action at step 126. Although it is conceivable that the tongue action may be detected at step 126 simply by analyzing the signal corresponding to changes in air pressure without additional data processing, it is preferable that the tongue action detection process of step 126 include data processing in conjunction with the signal analysis.

Figure 5:
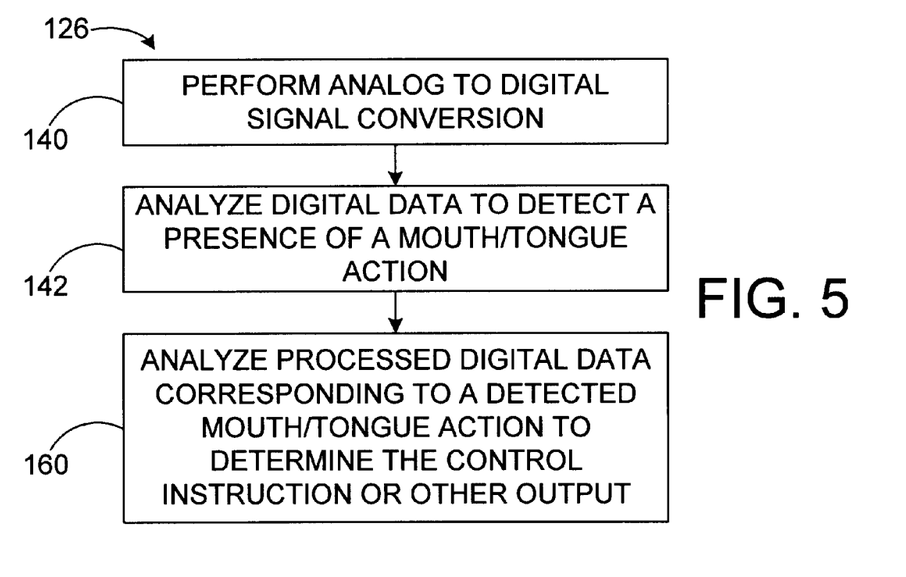
FIG. 5 is a flow chart diagram illustrating a method of processing an electrical signal corresponding to the air pressure for detecting a thought.
Figure 6:
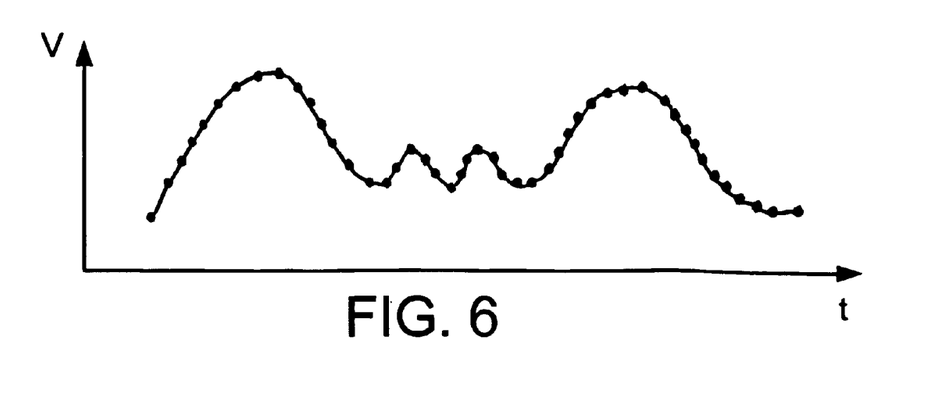
FIG. 6 is a graph illustrating the conversion of an analog electrical signal to digital signal data according to the present invention.

A method of analyzing and processing the electrical signal which corresponds to the monitored pressure is illustrated in FIG. 5. The electrical signal, which is an analog signal as illustrated in FIG. 2d, is converted into a digital signal at step 140, as illustrated in FIG. 6. As is well known by those skilled in the art, an analog signal may be converted into a digital signal by sampling the analog signal at a selected frequency and identifying the signal amplitude at each sampling point. Each sampled data point is then saved as a digital word in a memory and used for further analysis. In FIG. 6, a sampled analog signal is illustrated in which the dotted line illustrates the exemplary analog signal for a particular time period and the plurality of points on the dotted line represent sampled amplitude values which are saved in the memory. It is desirable that the sampling frequency be sufficient to capture enough data points to adequately represent the analog signal. As an example, the sampling rate of the may be 32 KHz and the total signal time length to be analyzed may be 2048 mSec. Alternatively, however, other sampling rates and data acquisition time frames may be utilized and such variations are contemplated as falling within the scope of the present invention.

Figure 7:
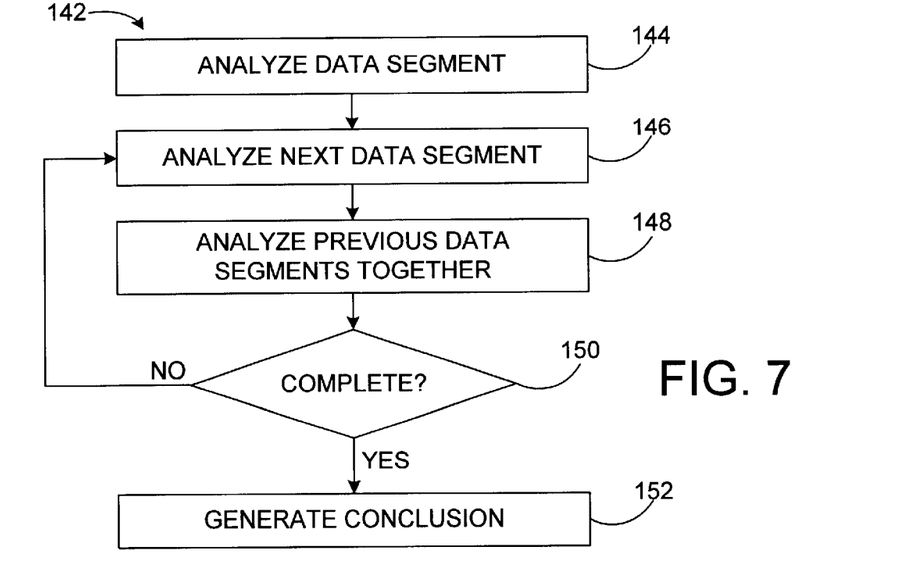
FIG. 7 is a flow chart diagram illustrating a method of analyzing the digital signal data according to the present invention.
Figure 8:
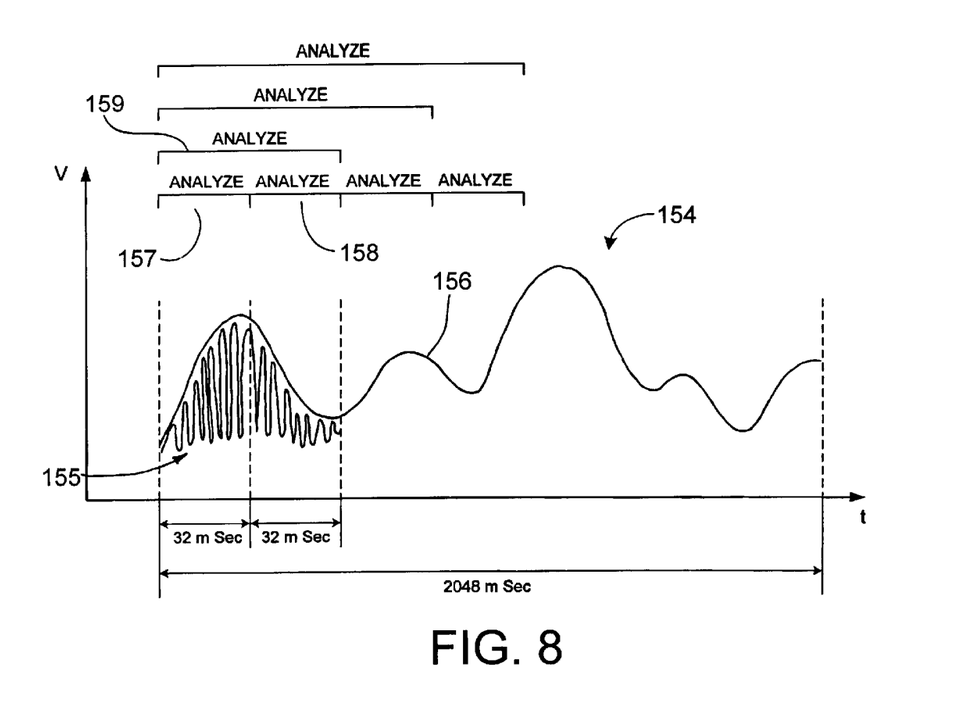
FIG. 8 is a graph illustrating a method of analyzing the digital signal data with the flow chart of FIG. 7 according to the present invention.

Once the analog signal has been converted into digital signal data at step 140, the digital data is analyzed and processed by, for example, a signal processor to detect the presence of a tongue action at step 142. The analysis and processing of the data may be performed in a plurality of segments, for example, as illustrated in FIGS. 7 and 8. As illustrated in FIG. 7, a first data segment is analyzed at step 144, followed by the analysis of a second data segment at step 146. Once various data segments have been analyzed separately, the data segments are analyzed together at step 148. If all the data segments have not yet been analyzed at step 150, the method 142 returns to step 146 and the next data segment is analyzed, after which all previous segments are then analyzed together at step 148. The process continues until all the data segments have been analyzed at step 150, thus allowing a conclusion to be generated using the analyzed data segments at step 152.

The data segment analysis may be seen graphically in FIG. 8, wherein digital signal data 154 is illustrated as being continuous for the sake of simplicity. The total length of data for analysis may be separated into 64 segments that are each 32 mSec in length. Note that the signal 154 contains both a high frequency component 155 and a low frequency component 156. Since data relating to a tongue action potentially may be found in either component or the tongue action data may span multiple data segments, the data segments may be analyzed separately as well as together. Thus, at step 144 of FIG. 7, the first data segment is analyzed (region 157), at step 146 the second data segment is then analyzed (region 158) and at step 148 both data segments are analyzed together (region 159). The process then continues for all the data segments; consequently, the data analysis of the present invention may analyze both the high frequency and low frequency signals to detect the tongue action since empirical testing has shown that signals of interest typically fall in the range of about 10 Hz to about 800 Hz. or in the range of about 20 Hz. plus or minus about 10 Hz.

Returning back to FIG. 5, once the data considered to be tongue action data has been found in the pressure data at step 142, subsequent analysis is performed to determine the type of tongue action at step 160. Such analysis includes feature extraction and analysis using a neural net trained to recognize respective signals/features of such signals. If the neural net determines that the signal represents a tongue action of a particular character, then it provides an output or effects the production of an output representative thereof for use as described herein. Alternatively, however, other techniques may be utilized to identify the tongue action type once the tongue action is detected and any such technique is contemplated as falling within the scope of the present invention.

Figure 9:
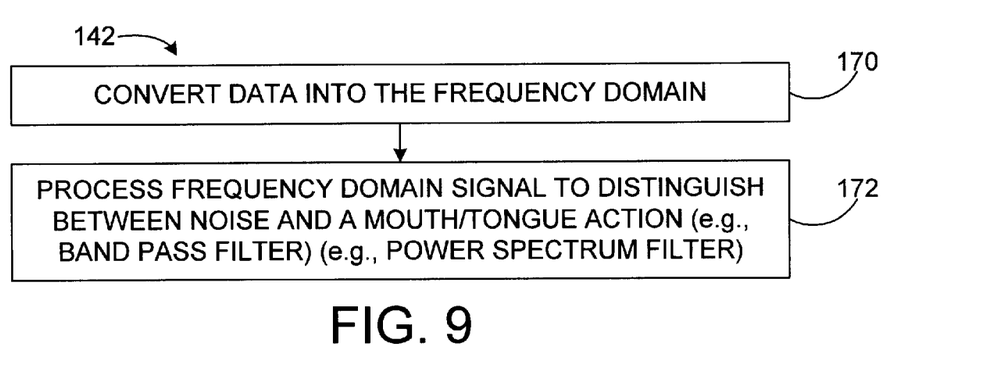
FIG. 9 is a flow chart diagram illustrating a method of processing the digital signal data according to the present invention.

One exemplary method of analyzing the digital signal in data segments is illustrated in FIG. 9. For each data segment of 32 mSec, the data is converted from the time domain to the frequency domain at step 170 using, for example, a Fast Fourier Transform (FFT) as is well known by those skilled in the art. As is well known, a time domain signal f(t) is linked with the frequency domain f(jω) according to the following equation:

$$F(f(t)) = \int f(t)e^{-j\omega t} dt = f(j\omega),$$

wherein F(f(t)) is a traditional Fourier transform. As is well known by those skilled in the art, a Fast Fourier Transform is related to the traditional Fourier transform since the Fast Fourier Transform is an efficient algorithm for computing discrete Fourier transforms. After the digital signal data is converted into the frequency domain via the Fast Fourier Transform, the frequency domain data is processed to distinguish data relating to tongue actions from noise data at step 172. As is well known by those skilled in the art, the separation of data from noise is often simplified in the frequency domain because unlike noise, the data signal has some physical characteristics. Though the data signal in the time domain has an amplitude which is less than the noise, the data signal has a greater amplitude than the noise in the frequency domain. Therefore the Fast Fourier Transform is a typical method for noise separation.

The details surrounding the data processing of the digital signal data may be accomplished through a variety of data processing techniques as is well known by those skilled in the art and any data processing methodology is contemplated as falling within the scope of the present invention. Although many different data processing methodologies may be employed, the preferred methodology is disclosed below in conjunction with the following method and system.

Figure 10:
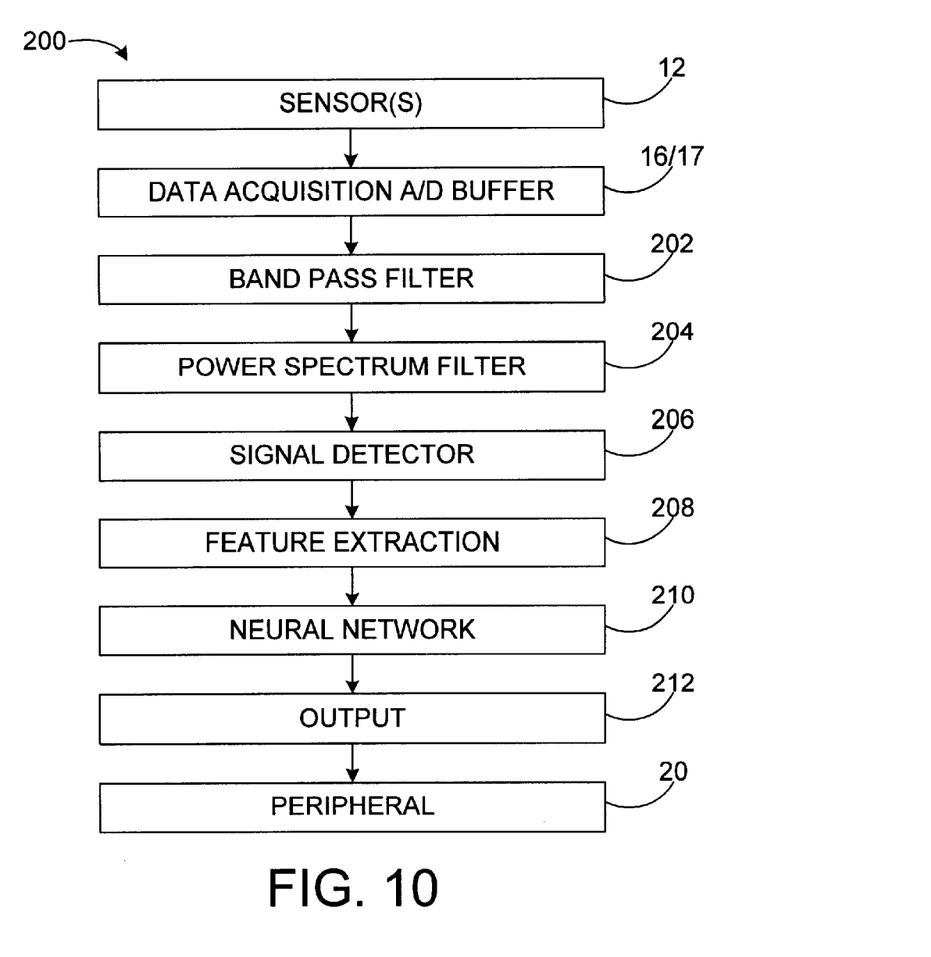
FIG. 10 is a system diagram showing a system including parts and functions of the invention.

Turning to FIG. 10, the system 200 and method of the invention are depicted. One or more sensors 12 sense air pressure from the ear(s) of the user. The analog signal(s) from the sensor(s) is provided via a data acquisition card, analog to digital converter, and buffer 16/17 to the processor 18. The signal received from the sensors is substantially continuous at least over respective time periods while the tongue is being moved; and, therefore, the buffer 17 is able to store sufficient portions of the signal for analysis by the processor 18.

The processor 18 includes a band pass filter 202, power spectrum filter 204, signal detector 206, feature extraction portion 208, and neural network 210. The system 200 also includes an output 212 which may be coupled to a desired output peripheral 20.

Figure 11:
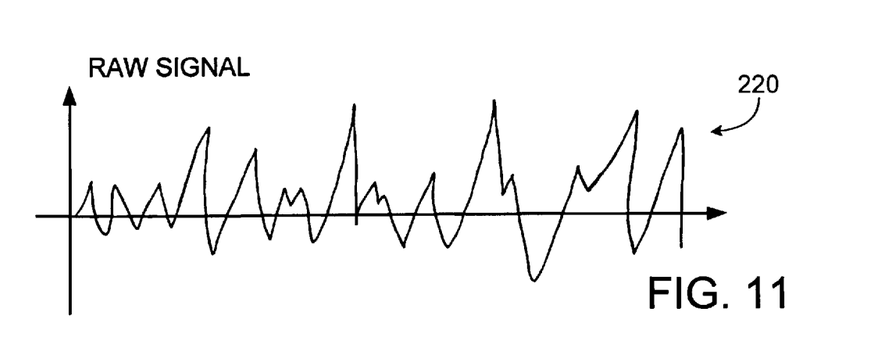
FIG. 11 is a graph representing exemplary raw signal information detected by a sensor used in the invention to detect air pressure representative of a mouth action.

Summarizing operation of the overall system 200, the sensor(12) and data acquisition, A/D, and buffer 16/17 supply a signal to the band pass filter 202. An example of a raw data or raw signal supplied to the band pass filter 202 is illustrated at 220 in the graph of FIG. 11. The raw signal is presented to the band pass filter and is operated on by the band pass filter in the frequency domain using fast Fourier transform techniques. The fast Fourier transform transforms the digital signal to the frequency domain. In the band pass filter frequencies that are above or below the frequency range representing tongue action, for example, are removed from the signal. The frequencies which are above and below the frequency range of interest typically are due to noise. An example of the signal after being filtered by band pass filtration is illustrated at 222 in the graph of FIG. 12. Various band pass filters may be used to provide the band pass filtration to strip from the signal frequencies above and below the desired frequency range.

Figure 12:
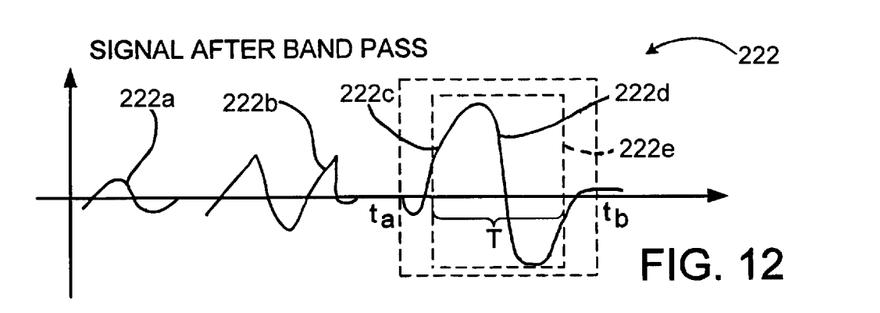
FIG. 12 is a graph of frequency filtered signal information of FIG. 12, the frequency filtering to remove noise, for example.
Figure 13:
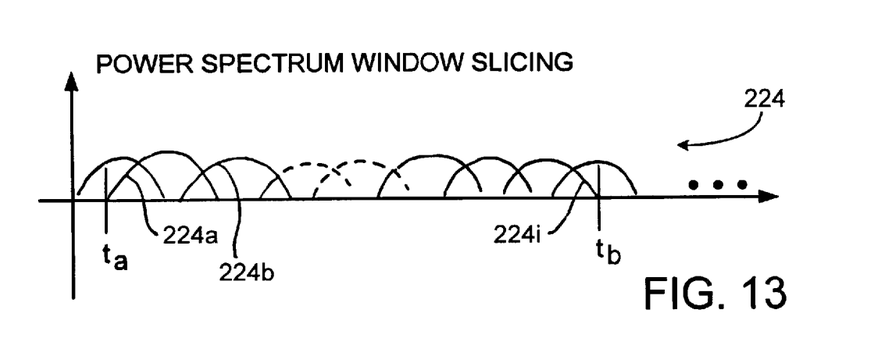
FIG. 13 is a graph representing windows in which a power spectrum of the curve of FIG. 12 for use to locate in time signals representative of a head action.

Portions of the signal represented at 222, such as portions 222a and 222b may not be representative of tongue action, e.g., since they are relatively low power and, therefore, still may be noise. Therefore, the power spectrum filter 204 does a further filtration according to power of the various portions of the signal to determine portions which are due to tongue action and, accordingly, should be considered for further analysis. The power filtration may be carried out by slicing the signal of FIG. 12 to multiple windows or segments, such as those represented at 224a, 224b, . . . 224i in FIG. 13. It will be appreciated that the graph of FIGS. 12 and 13 are of different scales. Thus, the windows 224a–224i slice a time frame between times $t_a$ and $t_b$, which is the same time frame between times ta and tb illustrated for the signal portion 222c in FIG. 12.

Power filtration suppresses or eliminates those frequencies where the power of the signal does not exceed a prescribed threshold or value and, thus, likely represent noise. By eliminating those noise components the signal representing the tongue action can be found. To perform the power filtration, for example, a power spectrum for the signal is calculated using the following formula:

$$P_f = \text{Mag}_f^2 + \text{Phase}_f^2$$

where $f = F_0 \ldots F_j$, and $[F_0; F_i]$ represent the frequency range in which the signal resulting from tongue action is expected.

Figure 14:
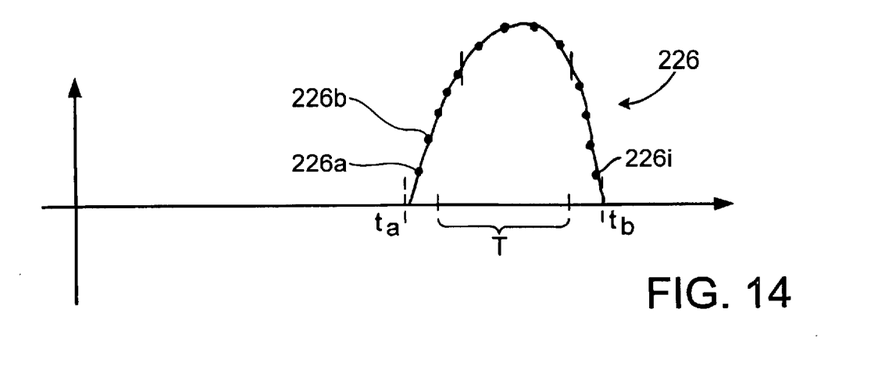
FIG. 14 is a graph of such power spectrum.

In words, the power is a function of the magnitude squared plus the phase squared. The power as calculated above for respective windows 224a, 224b ... 224i is reconstructed to make a graph 226 shown in FIG. 14. The graph 226 shows values 226a, 226b ... 226i from the mentioned computation. The curve 226 is relatively smooth and it represents power spectrum where a signal caused by tongue action may be found in the graph 222 of FIG. 12. Usually the signal caused by tongue action is of relatively high power and occurs in time approximately at the middle of the graph 226, e.g., over the time frame T shown in FIG. 13. It is the time at which this time frame occurs and the duration of it that detects the signal or locates when in time the signal 222 represents the tongue action. Therefore, the signal detector component 206 of the system 200 in effect is the combination of the graphs of FIGS. 12 and 13 and the analysis just described to provide the signal detection function. The time frame T also is shown in the graph of FIG. 12 and, thus designates that portion 222d (in the illustrated blocked window 222e) of the signal 222c which is to be considered produced by the tongue action.

The signal portion 222d or at least a feature of that signal then may be supplied to the neural network 210. Using feature extraction principles a feature of the signal portion 222d is supplied to the neural network. In the neural network 210 the feature is compared with other features on which the neural network has been trained. Training of neural networks is a well known procedure. The neural network can determine whether an input feature, such as that representative of the signal portion 222d, is an acceptable match or correlates acceptably to the training of the neural network; and, if affirmative, then the neural network causes production of the output 212. The output 212 may be an electrical signal which is analogous to the type of signal produced by a computer mouse, joystick or other device. Thus, a tongue action whereby the tongue of the user is moved from the front bottom left of the mouth to the back top right of the mouth may cause the production of an output signal analogous to a movement of a mouse from the lower left to the upper right of a mouse pad. As another example, movement of the tongue from the left front of the mouth to the right front of the mouth may result in a signal analogous to a mouse being moved from left to right; and so forth.

The feature which is extracted from the signal 222, for example, may be features which designate some characteristic or feature which differentiates the curve representing the signal from other things. Various features are used in feature extraction methods, which are well known. In the present invention an exemplary feature is the smoothed power spectrum of the signal portion 222d. Other features may be the logarithm of the power spectrum, the power spectrum itself, etc.

The neural network 210 may be a conventional neural network trained in a typical fashion. The neural network 210 can compare the feature of the signal portion 222d with its training and can determine whether the feature is more like one trained feature or another trained feature. If the input feature of signal portion 222d is sufficiently like one trained feature, then the neural network causes production of an appropriate signal at the output, as was described above, for example. If the input feature is not sufficiently like any of the trained features or is relatively similar to two or more trained features, then the neural network will not cause the output to produce an output signal, for the uncertainty may otherwise cause production of an undesirable output signal.

As was described above, if two sensors 12 are used, then the system 200 may operate sequentially on each signal from respective sensors or may include parallel processing capability so that the signals from both sensors can be processed substantially simultaneously. The output 212 may reflect the results of signal analysis of the signals originating from both sensors and may be used to provide an output signal at the output 212 that reflects in effect three dimensional data.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A method of producing a control signal, comprising the steps of:

sensing an air pressure pattern produced by an ear of a person, the air pressure pattern resulting from a voluntary physical action of the person;

converting the air pressure pattern into an electrical output signal;

generating a control instruction from the electrical output signal, the control instruction corresponding to the voluntary physical action; and controlling an output peripheral with the control instruction.

2. The method according to claim 1, further comprising the step of placing a microphone adjacent the ear, the microphone acting to convert the air pressure pattern into the electrical output signal.

3. The method according to claim 1, wherein the control instruction is used to control a computer, machine or other item of equipment.

4. The method according to claim 1, further comprising the steps of:

placing an air pressure sensor near the ear of the person to sense air pressure patterns associated with each of a plurality of unique voluntary physical actions by the person;

recording a resulting output signal for each unique physical action; and generating a set of control instructions, each control instruction corresponding to a corresponding one of the output signals.

5. The method according to claim 1, further comprising the steps of:

separating the electrical output signal into a plurality of data segments;

analyzing a first data segment for the detection of a particular physical action having a known electrical signal paftem;

analyzing a second data segment for the detection of the particular physical action; and analyzing at least two successive data segments for the detection of the particular physical action.

6. The method according to claim 1, further comprising processing the electrical output signal by carrying out the steps of:

(a) separating the electrical output signal into a plurality of data segments;

(b) analyzing a first data segment for the detection of a physical action;

(c) analyzing a next data segment for the detection of a physical action;

(d) analyzing all the analyzed data segments together for the detection of a physical action; and (e) repeating steps (c) and (d) until all the data segments are analyzed.

7. The method according to claim 1, wherein air pressure patterns are monitored adjacent each ear of the person to derive a representation of the physical action from the electrical output signals corresponding to the air pressure pattern sensed at each ear.

8. The method according to claim 1, further comprising the step of analyzing the electrical output signal for a match against one of a set of predetermined output signal patterns.

9. The method according to claim 1, wherein the physical action includes a motion with a head of the person.

10. The method according to claim 1, wherein the physical action is associated with an oral cavity of the person.

11. The method according to claim 1, wherein the physical action includes a movement of a tongue of the person.

12. The method according to claim 1, wherein the physical action includes a respiratory action of the person.

13. The method according to claim 1, further comprising the step of determining whether the electrical output signal correlates to one of a set of trained patterns using a neural network.

14. The method according to claim 1, wherein the voluntary physical action is a non-vocal movement of the tongue of the person.

15. A control system, comprising:

an air pressure sensor for detecting an air-pressure pattern produced by an ear of a person while the person makes a non-vocal voluntary physical action and for producing an electrical output signal corresponding to the detected air pressure pattern; and processing circuitry electrically coupled to the air pressure sensor and for discerning a pattern from the electrical output signal and generating a control instruction corresponding to the voluntary physical action, the control instruction adapted to control an output peripheral.

16. The control system according to claim 15, wherein the processing circuitry identifies the control instruction from a plurality of specific control instructions.

17. The control system according to claim 15, further comprising the output peripheral coupled to the processing circuit to be controlled by the control instruction.

18. The control system according to claim 17, wherein the output peripheral is selected from a computer, a display, a machine, a robot, a gaming device and a wheelchair.

19. The control system according to claim 15, wherein the processing circuitry analyzes the output signal for a match against one of a set of predetermined output signal patterns.

20. The control system according to claim 15, wherein the air pressure sensor is a microphone.

21. The control system according to claim 20, wherein the microphone is removably attachable near the ear of the person with support member and the microphone has a housing to reduce the detection of extraneous pressure variations.

22. The control system according to claim 15, wherein the processing circuitry includes a neural network for determining whether the pattern correlates to one of a set of trained patterns.

23. The control system according to claim 15, wherein air pressure patterns associated with each of a plurality of physical actions by the person are detected and the resulting output signals for each physical action are recorded by the processing circuitry, the processing circuitry generating a set of control signals, each control signal corresponding to at least one of the plurality of output signals.

24. The control system according to claim 15, wherein the processing circuitry:

separates the electrical signal into a plurality of data segments;

analyzes a first data segment for the detection of a particular physical action having a known electrical signal pattern;

analyzes a second data segment for the detection of the particular physical action; and analyzes at least two successive data segments for the detection of the particular physical action.

25. The control system according to claim 15, wherein the processing circuitry:

(a) separates the electrical signal into a plurality of data segments;

(b) analyzes a first data segment for the detection of a physical action;

(c) analyzes a next data segment for the detection of a physical action;

(d) analyzes all the analyzed data segments together for the detection of a physical action; and (e) repeats steps (c) and (d) until all the data segments are analyzed.

26. The control system according to claim 15, wherein a second air pressure sensor monitors air pressure patterns adjacent a second ear of the person and the processing circuitry derives a three dimensional representation of the physical action from output signals from both of the air pressure sensors.

27. The control system according to claim 15, wherein the physical action includes a motion with a head of the person.

28. The control system according to claim 15, wherein the physical action is associated with an oral cavity of the person.

29. The control system according to claim 15, wherein the physical action includes a movement of a tongue of the person.

30. The control system according to claim 15, wherein the physical action includes a respiratory action of the person.

31. The control system according to claim 15, wherein the non-vocal voluntary physical action is a non-vocal movement of a tongue of the person.

* * * * *